United States Patent
Benchetrit

(10) Patent No.: US 6,916,326 B2
(45) Date of Patent: Jul. 12, 2005

(54) GASTROPLASTY RING THAT CAN BE LOOSENED

(75) Inventor: Salomon Benchetrit, Caluire (FR)

(73) Assignee: Compagnie Europeenne d'Etude et de Recherche de Dispositifs pour l'Implantation par Laparoscopie, Vienne (FR)

( * ) Notice: Subject to any disclaimer, the term of this patent is extended or adjusted under 35 U.S.C. 154(b) by 305 days.

(21) Appl. No.: 10/168,583

(22) PCT Filed: Dec. 21, 2000

(86) PCT No.: PCT/FR00/03651

§ 371 (c)(1),
(2), (4) Date: Nov. 4, 2002

(87) PCT Pub. No.: WO01/45597

PCT Pub. Date: Jun. 28, 2001

(65) Prior Publication Data

US 2003/0120288 A1 Jun. 26, 2003

(30) Foreign Application Priority Data

Dec. 21, 1999 (FR) .............................. 99 16201

(51) Int. Cl.[7] .............................................. A61B 17/04
(52) U.S. Cl. ..................... 606/151; 604/909; 606/157
(58) Field of Search ................... 606/151, 157; 604/909

(56) References Cited

U.S. PATENT DOCUMENTS

| 4,592,339 A | * | 6/1986 | Kuzmak et al. | ............. 128/899 |
| 4,701,163 A | | 10/1987 | Parks | ........................ 604/178 |
| 5,074,868 A | * | 12/1991 | Kuzmak | ...................... 606/157 |
| 5,160,337 A | * | 11/1992 | Cosman | ...................... 606/130 |
| 5,449,368 A | * | 9/1995 | Kuzmak | ...................... 606/157 |
| 5,601,604 A | * | 2/1997 | Vincent | ...................... 606/216 |

FOREIGN PATENT DOCUMENTS

| DE | 9014048 | 12/1990 | .......... A61B/17/12 |
| DE | 19751733 | 12/1998 | .......... A61B/17/12 |

* cited by examiner

Primary Examiner—Gary Jackson
(74) Attorney, Agent, or Firm—James W. Kayden; Thomas, Kayden, Horstemeyer & Risley

(57) ABSTRACT

A gastroplasty ring having a single control is provided and includes a flexible strip with two ends for being closed around the stomach by a closure system so as to reduce the diameter of the opening of the stoma. The strip may have an annular compression chamber of adjustable volume and of substantially constant section connected by an adjustment catheter to a device for adjusting the internal pressure in the chamber so as to adjust its diametral expansion. The closure system may be used for reversibly locking and loosening the ring, and for releasing the diameter of the ring momentarily by relative displacement between the two ends, while continuously forming a closed loop around the stomach. The ring constitutes a gastric implant for treating obesity.

12 Claims, 2 Drawing Sheets

GASTROPLASTY RING THAT CAN BE LOOSENED

TECHNICAL FIELD

The present invention relates to the technical field of surgical implants for treating obesity by implanting a flexible gastric strip for constricting the stomach of a patient, said gastric strip being provided with an annular compression chamber of variable volume that is adjustable by means of an adjustment catheter connected to a control and adjustment device implanted in the body of the patient.

The present invention relates to a gastroplasty ring formed by a flexible strip for passing around the stomach and being closed substantially near and by means of its two ends, using a closure system to reduce the diameter of the stoma opening, said strip including an annular compression chamber of adjustable volume that is connected by an adjustment catheter to a device for adjusting the internal pressure of said chamber so as to adjust its diametral expansion.

PRIOR ART

For patients suffering from extremely severe obesity (morbid obesity), i.e. for patients whose weight exceeds the ideal weight by at least 50 kilograms, for example, it is absolutely essential to operate surgically on such patients in order to avoid not only a series of health problems that stem from such obesity, but also to avoid certain and imminent death of such patients.

It is accepted that patients suffering morbid obesity have life expectancy that is significantly reduced, by at least ten to fifteen years, while also giving rise to severe psychological problems. Furthermore, a whole series of associated health phenomena are involved, having an effect on the appearance of cardiovascular disease hypertension, diabetes, and severe arthritis, in particular.

It has also been observed that treatment based on a severe diet combined with a series of physical exercises associated with a change in behavior, in particular eating behavior, are relatively ineffective in such cases of morbid obesity, even though such methods of treatment are the most healthy.

That is why effective long-term treatment of morbid obesity can involve surgical treatment.

In general, surgical treatment techniques can be divided into those which cause food to be absorbed poorly, i.e. shortening the conventional path followed by food and digestive juices, and techniques that make use of gastric restriction, i.e. reducing the size of the stomach.

By way of example, surgical techniques that rely on poor absorption are those that imply a technique of bypassing the small intestine or those, which separate the paths followed by food and digestive juices. The bypass surgical technique gives rise to severe complications, such that that technique is now used only very rarely. The surgical technique whereby the path followed by the alimentary bolus is separated from that of the digestive juices does not give rise to particular complications, but it does require major surgery, and in particular it implies partial gastrectomy.

That is why present trends are towards using surgical techniques that implement gastric restriction to reduce food intake.

In conventional manner, such techniques make use of gastroplasty rings implanted around the stomach to reduce its size and the diameter of its passage (stoma).

Most known gastroplasty devices, for example the device described in U.S. Pat. No. 5,074,868, make use of a flexible strip made of elastomer material that is implanted around the stomach and then tightened and closed to form a loop of fixed diameter by means of a closure system. The body of the flexible strip includes a variable volume compression cavity or chamber that is connected by an adjustment catheter to a device for adjusting the internal pressure of the chamber so as to vary the internal diameter of the loop and thus modify or adjust the diameter of the stoma by injecting or extracting a volume of liquid into or from the chamber. Such an operation of adjusting the inside diameter of the ring is performed by means of conventional control devices including a miniature unit implanted directly beneath the skin of the patient and provided with a self-closing membrane through which the doctor injects or withdraws liquid by means of a syringe.

Utility model DE-G-90 14048 describes a partially annular system specifically designed and adapted to totally closing blood vessels, and its teaching is not directly transposable to compressing the stomach which must be done under full control.

The closure system of U.S. Pat. No. 5,075,868 makes use of suture thread for suturing together the two strands of the flexible strip constituting the ring.

Such a device generally gives satisfaction, but like most known systems it suffers from drawbacks associated essentially with the difficulty of any surgical operation that may need to be performed after the gastroplasty implant has been into place. In spite of the possibility of modifying the diameter of the ring to some extent without a surgical operation by means of the above-mentioned miniature unit, it turns out that implanting such gastric implants can be accompanied by phenomena of intolerance, e.g. can be accompanied by vomiting, associating with the diameter of the stoma being reduced excessively, or they can be associated with the implant being ineffective in its action because the diameter of the stoma is too large, or indeed they can be associated merely with local or general inflammation or infection or discomfort.

That is why it is often necessary to operate surgically again either to relieve the patient or to modify or change a previously implanted gastroplasty ring. Such surgical operations are particularly difficult and further require the surgeon to cut either the ring, or as in the case of U.S. Pat. No. 5,074,868, the suture thread so as to open the ring completely and then change it or replace it.

Such operations are awkward to perform, poorly tolerated by the patient, and expensive, particularly in that they imply the destruction of an implant and its replacement. In addition, in the case of U.S. Pat. No. 5,074,868, the device for assisting in cutting the suture makes the surgical implant relatively complex to manufacture and make up, without genuinely providing much real help during the operation.

SUMMARY OF THE INVENTION

Consequently, the object given to the invention is to propose a novel gastroplasty ring making it possible to remedy the various drawbacks mentioned above and capable of facilitating any subsequent surgical operations after the implant has been implanted, without requiring the implant to be replaced, and with the implant in any event being of particularly simple design that is easy to make.

Another object of the invention is to propose a novel gastroplasty ring capable in simple and reliable manner of reversibly closing the loop that constitutes the ring.

Another object of the invention is to propose a novel gastroplasty ring suitable for providing simple and reliable means for adapting the diameter of the ring to each particular surgical situation.

Another object of the invention is to propose a novel gastroplasty ring suitable for presenting a plurality of implantation diameters.

Another object of the invention is to propose a novel gastroplasty ring making it possible to reduce the discomfort felt by the patient while nevertheless being firmly held in place by the loop.

Another object of the invention is to propose a novel gastroplasty ring that is particularly easy to manufacture while also providing excellent general strength.

The objects given to the invention are achieved by means of a gastroplasty ring formed by a flexible strip suitable towards its two ends for being closed around the stomach by a closure system so as to reduce the diameter of the opening of the stoma, said strip having an annular compression chamber of adjustable volume and of substantially constant section connected by an adjustment catheter to a device for adjusting the internal pressure in said chamber so as to adjust its diametral expansion, the ring being characterized in that the closure system includes means for reversibly locking and loosening the ring, said means comprising male means and female means forming a cavity in which or against which the male means can expand and become locked in reversible manner, thus making it possible, starting from the position in which the diameter of the ring is locked, to release the diameter of the ring momentarily by relative displacement between the two ends, while nevertheless continuously forming a closed loop around the stomach.

BRIEF SUMMARY OF THE DRAWINGS

Other objects and advantages of the invention will appear better on reading the following description and from the accompanying drawings given purely for illustration and information, in which.

BEST MANNER OF PERFORMING THE INVENTION

Figure 1:
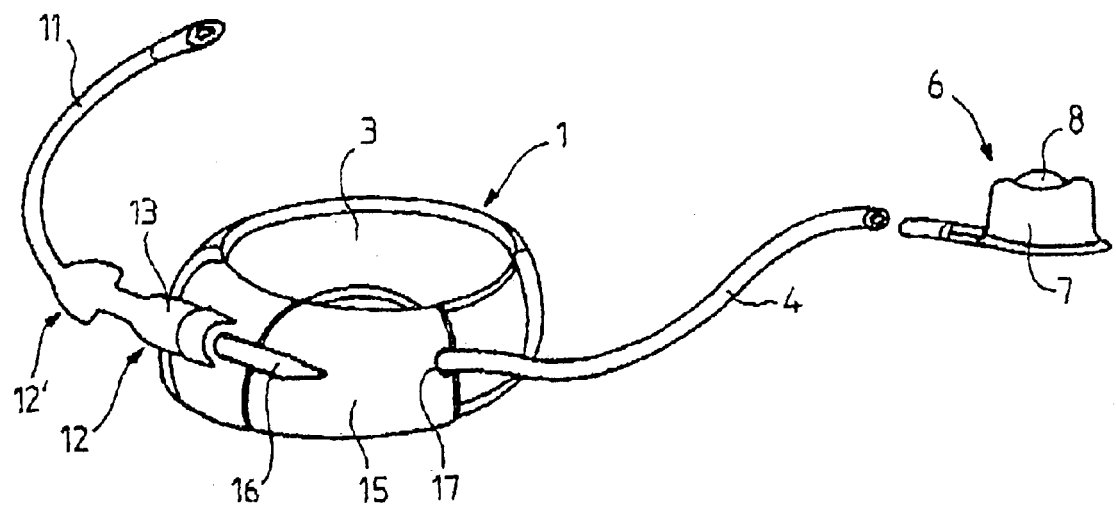
FIG. 1 is a diagrammatic perspective view of an embodiment of a gastroplasty ring of the invention shown in the closed position.
Figure 2:
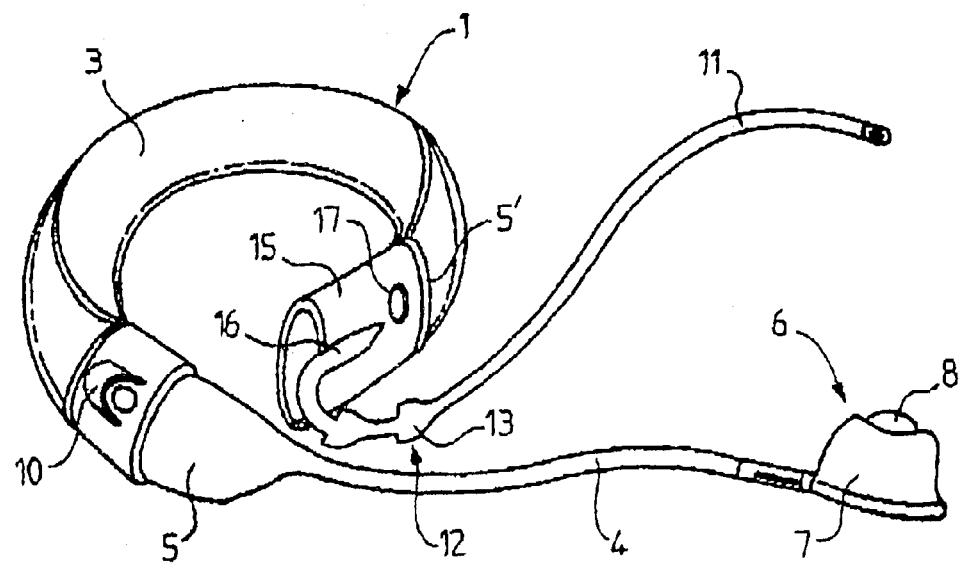
FIG. 2 is a diagrammatic perspective view of an embodiment of a gastroplasty ring of the invention in the open position prior to being implanted.

FIGS. 1 and 2 show a preferred embodiment of a gastroplasty ring of the invention formed by a flexible strip 1 made, for example, by thermoforming an elastomer material for surgical use. The strip 1 defines an internal compression chamber 2 of substantially constant section that preferably extends substantially over its entire length, the chamber being defined by the walls 3 of the flexible strip 1 and by two end zones 5 and 5'. In its position when implanted around the stomach of a patient, as shown in FIG. 1, the compression chamber 2 thus forms an annular compression chamber of section and profile that are adapted to avoid forming any pinch zones that could nip the walls of the stomach. This implies in particular that it has a contact surface with the stomach that is continuous and uniform and that an annular compression zone is formed that is almost perfect, excluding in particular any droplet shape that might damage cellular tissue.

As is well known in the prior art, the compression chamber 2 defines a closed volume inside the gastroplasty ring, for the purpose of forming a volume that is adjustable so as to adjust the diametral expansion of the ring while it is in place in order to adapt it to each particular surgical situation.

In conventional manner, the diametral expansion of the gastroplasty ring of the invention is adjusted by an adjustment catheter 4 formed by a tubular element of elastomer material extending the free end 5 of the compression chamber 2 so as to connect said chamber to a device 6 for adjusting the internal pressure of said chamber.

As is well known to the person skilled in the art, the adjustment device 6 can be formed by a miniature unit 7 that is implanted beneath the skin of the patient. By way of example, the miniature unit 7 has a self-sealing membrane 8 on top for being pierced by a syringe so as to inject or withdraw a certain quantity of fluid (e.g. distilled water) for the purpose of varying the volume of the compression chamber 2, to adjust the volume of the chamber and thus obtain the desired internal diameter for the ring. Since such a device is well known to the person skilled in the art, it is not described in greater detail herein.

The gastroplasty ring of the invention also has a closure system enabling it to be closed and serving to hold the gastroplasty ring looped in position around the stomach.

According to an important characteristic of the invention, the closure system of the invention includes means for reversibly locking and loosening the ring, making it possible starting from the closed position shown in FIG. 1 where the ring is looped with a locked diameter, to release its diameter momentarily by allowing the two ends of the ring to move relative to each other, while nevertheless continuously forming a closed loop around the stomach.

Providing this technical function makes it possible to reduce the severity and the extent of any subsequent surgical operations after an implant has been put into place by avoiding the need to section and destroy the installed gastroplasty ring, with this function making it possible to leave the ring in place while merely momentarily increasing its diameter without destroying the loop of the ring, thus making it possible subsequently to retighten the ring so as to return it to the closed position as shown in FIG. 1.

Figure 3:
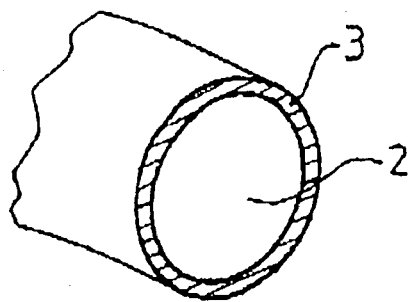
FIG. 3 is a fragmentary cross-section view showing a detail of the section of the gastroplasty ring of the invention.

In a preferred variant of the invention, as shown in FIGS. 1 to 3, the gastroplasty ring of the invention includes a closure system that comprises:

male means and female means secured to the strip 1, e.g. situated substantially in the vicinity of respective ones of the two ends 5 and 5', the male and female means being mounted on the strip, i.e. extending its two ends 5 and 5' so that during mutual connection thereof the strip 1 is closed to form a loop; and reversible locking and loosening means are mounted on the male means so as to be suitable for sliding in the female means 10 between a locking position and at least one loosened position, while nevertheless enabling the loop to be maintained.

The preferred embodiment shown in the figures has female means in the form of an eyelet 10 provided at the periphery of the strip 1 in a position adjacent to the end 5. The male means is formed by an inflatable catheter 11 made of biocompatible elastomer material for threading through the eyelet 10 in the closed ring position and also for serving as guide means.

The reversible locking and loosening means are connected to the inflation catheter 11 and comprise a deformable zone 12 suitable for forming a projection 13 when the pressure inside the inflation catheter 11 is increased, said projection 13 bearing in or against the female means 10 to lock the ring in the closed position. The projection 13 returns to its rest shape if the pressure inside the inflation catheter 11 returns to normal, thereby allowing the said catheter to slide and be guided freely through the eyelet 10, thus loosening the loop.

The reversible locking and loosening means are advantageously formed on the inflation catheter 11 (FIGS. 1, 2, 5) and are intended to co-operate with the eyelet 10 so that when the eyelet 10 is connected to the inflation catheter 11, the ring is locked reversibly and is capable of being loosened.

In a particularly advantageous version of the invention, the reversible deformation zone 12 is formed by at least one zone 13 of weakness suitable firstly for locally forming a projection in the event of the pressure inside the inflation catheter 11 increasing, said projection then bearing in or against the eyelet 10 to lock the ring in the closed position, and suitable secondly for returning to its rest position which then corresponds substantially to the normal diameter of the catheter 11 when pressure returns to normal so as to allow the inflatable catheter 11 to slide freely in the eyelet 10, thereby allowing the loop to be loosened. The weak zone 13 can extend over the entire peripheral section of the catheter 11 to form a bulb, or over a fraction only thereof so as to form a simple projecting dome.

Advantageously, the deformable zone 12 can be constituted by a section of the inflation catheter 11 having elastomer material constituting the inflatable catheter 11 presenting hardness which is locally less than the general hardness of the inflation catheter 11. Under such circumstances, the inflation catheter 11 is connected to an external device for being pressurized by means of a fluid (air or liquid), and the zone 12 tends to form a balloon 13 of diameter greater than the diameter of the eyelet 10, thereby locking the diameter of the ring.

Naturally, and in a variant, a gastroplasty ring of the invention could have a plurality of weak zones 12 spaced apart in optionally regular manner along the inflation catheter 11 to make up a gastroplasty ring capable of occupying a plurality of fixed diameters when in position. Advantageously, the inflation catheter 11 has two weak zones 12 and 12'.

In this preferred embodiment, the locking and loosening means make use of fluid means (pneumatic or hydraulic, air, fluid, or liquid, for example) that perform the reversible locking and loosening function.

Advantageously, the flexible strip 1 is provided at one end, e.g. at its end 5' opposite its end 5, with a hollow sleeve 15 extending the flexible strip 1, which hollow sleeve 15 has one end 16 of the inflatable catheter 11 fixed thereto. The hollow sleeve 15 also has an opening 17 provided in one of its face (preferably an outside face) so as to enable the other end 5 of the flexible strip 1 to be inserted into said sleeve in the closed position with the adjustment catheter 11 then passing through the opening 17 so as to loop the ring (FIG. 2). This structural disposition ensures that closure is reliable and long lasting, while also enabling the compression chamber 2 to extend over the entire perimeter over which the stomach is constrained.

As already described above, the eyelet 10 is advantageously placed at a distance from the end 5 of the strip so as to create a free portion of the compression chamber 2 for insertion into the hollow sleeve 15 in order to enable the ring to be put into place in its looped position.

Advantageously, the flexible strip 1, the compression chamber 2, and the female means 10 form a single piece made out of the same elastomer plastic material, the adjustment catheter 4 and the inflation catheter 11 which are independent of each other being subsequently heat-sealed thereto.

Figure 5:
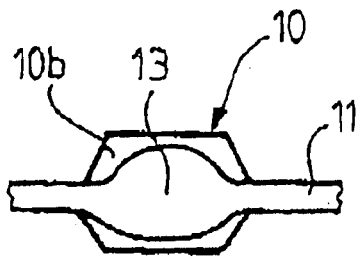
FIG. 5 is a fragmentary section view showing an implementation detail of a variant of a gastroplasty ring of the invention.

FIG. 5 shows a variant embodiment which differs from that of FIGS. 1 to 3 mainly in the female means 10, which are of a geometrical configuration for improving locking. In this variant, the eyelet 10 includes or is formed by a through cavity 10b in which the projection 13 or the balloon can expand and become reversibly locked in position depending on the pressure of the fluid. The cavity 10b can be situated to extend continuously from the annular section of the chamber 2 so as to form a ring that is regular and formed in full or in part by the hollow sleeve 15 or in line therewith on the other end of the ring.

Figure 4:
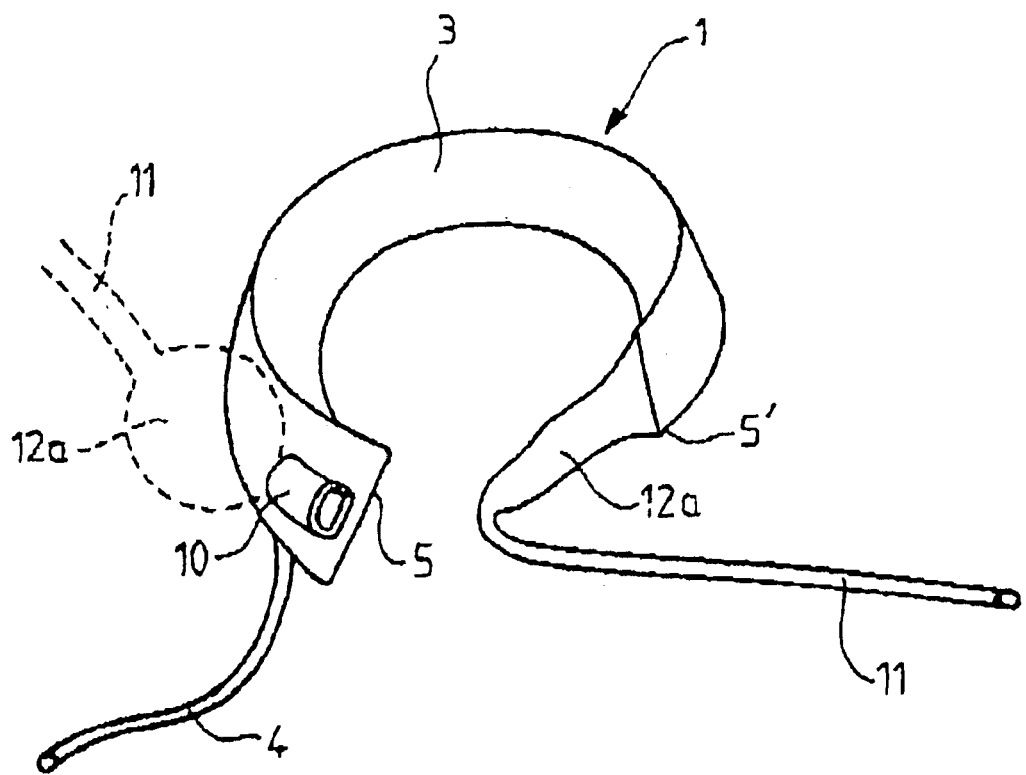
FIG. 4 is a perspective view showing a variant embodiment of the gastroplasty ring of the invention.

FIG. 4 shows another variant which differs from the preceding variant only in the configuration of the deformable zone 12. This zone is formed by a substantially oblong bag 12a secured to the flexible strip 1, e.g. extending the end 5' and fixed thereto. The inflation catheter 11 extends the bag 12a and is connected to the end portion thereof. While the ring is being closed, the catheter 11 and then the bag 12a are threaded through the eyelet 10, with the bag 12a (or the major fraction of its length) then projecting beyond the eyelet 10. When the inflation catheter 11 is pressurized, the bag 12a inflates as represented by dashed lines in FIG. 4, thus locking and closing the ring.

Making a gastroplasty ring as a single piece simplifies the method of manufacturing the ring and makes it possible to obtain a ring that avoids any risk of coming apart over time.

While the ring of the invention is being put into place around the stomach, it is in the position as shown in FIG. 2. The adjustment device 6 is initially disconnected and the surgeon passes the adjustment catheter 4 through the opening 17 so as to insert the end 5 in the hollow sleeve 15 (FIG. 1). Thereafter, the surgeon can use an inflation device (not shown in the figures) connected to the inflation catheter 11 to lock the ring in position after making sure that the weak zone 12 corresponding to the diameter desired for the implant is properly positioned relative to the eyelet 10. Thereafter, the surgeon can adjust the inside diameter of the ring by injecting or withdrawing the appropriate quantity of liquid by means of the adjustment device 6.

In the event of a subsequent surgical operation, the gastroplasty ring of the invention makes it possible to limit the operation to examining the outside surface of the implant in position by celioscopy or laparoscopy, merely using a camera for optical inspection. If circumstances require it, it is possible initially, merely by celioscopy, to reduce the pressure in the inflation catheter 11, thereby releasing the balloon 13 and allowing the inflation catheter 11 to slide through the eyelet 10 given that this catheter is of sufficient length. Such sliding is accompanied by momentary and partial loosening of the ring without it being necessary to perform major surgery on the patient. Thereafter, still merely by laparoscopic examination and intervention, it is possible to reclose and relock the ring in the closed position in very simple manner since the loop of the ring has never been undone.

SUSCEPTIBILITY OF INDUSTRIAL APPLICATION

The industrial application of the invention lies in designing and using gastroplasty rings.

What is claimed is:

1. A gastroplasty ring formed by flexible strip (1) suitable towards its two ends (5, 5') for being close around the stomach by a closure system (10, 10b, 11, 12, 12', 13) so as to reduce the diameter of the opening of the stoma, said strip having an annular compression chamber (2) of adjustable volume and of substantially constant section connected by an adjustment catheter (4) to a device (6) for adjusting the internal pressure in said chamber so as adjust its diametral expansion, the ring being characterized in that the closure system (10, 10b, 11, 12, 12', 13 ) includes means (10, 10b, 12, 12', 13) for reversibly locking and loosening the ring, said means comprising male means (11) and female means (10, 10b) forming a cavity in which or against which the male means (11) can expand and become locked in reversible manner, thus making it possible, starting from the position in which the diameter of the ring is locked, to release the diameter of the ring momentarily by relative displacement between the two ends (5, 5'), while nevertheless continuously forming a closed loop around the stomach.

2. A ring according to claim 1, characterized in that the locking and loosening means make use of a fluid means selected from the group comprising of air and a liquid.

3. A ring according to claim 1, characterized in that in the closure system (10–13 ):
   the male means (11) and the female means (10) are secured to the strip (1) and are mounted thereon to extend its two ends (5, 5') in such a manner that when they are mutually connected, the strip (1) is closed to form a loop; and
   the reversible locking and loosening means (12, 12', 13) are mounted on the male means (11) and are suitable for sliding in the female means (10) between a locking position and a loosening position.

4. A ring according to claim 1, characterized in that the female means is formed by an eyelet (10, 10b), the male means is formed by an inflatable catheter (11) for inflating through the eyelet (10, 10b), the reversible locking and loosening means being connected to the catheter (11) and including at least one deformable zone (12, 12') suitable firstly for forming a local projection (13) in the event of the pressure inside the catheter increasing, said projection hearing against the eyelet (10) to lock the ring in the closed position, and secondly for returning to its rest shape in the event of a return to normal pressure so us to allow the inflatable catheter (11) to slide freely in the eyelet (10, 10b) and loosen the loop.

5. A ring according to claim 4, characterized in that the deformable zone (12, 12') is a weak zone formed in the inflation catheter.

6. A ring according to claim 5, characterized in that the deformable zone (12) is formed by a bag (12a) extending the end (5') of the flexible strip (1) and to which the inflation catheter (11) is connected.

7. A ring according to claim 4, characterized in that the inflatable catheter (11) has two weak zones ( 12, 12') spaced apart along said catheter.

8. A ring according to claim 4, characterized in that the flexible strip (1) is provided at one end (5') with a hollow sleeve (15) to which one end (16) of the inflatable catheter (11) is fixed, said sleeve having an opening (17) so that the other end (5) of the strip (1) can be inserted into the sleeve (15) with the adjustment catheter (4) then passing through the opening (17) so as to loop the ring.

9. A ring according to claim 4, characterized in that the inflatable catheter (11) is connected to a device for pressurizing it and depressurizing it.

10. A ring according to claim 8, characterized in that the eyelet (10) is placed at a distance from one end (5) of the strip (1) so as to create a free portion of the chamber (2) suitable for being inserted in the hollow sleeve.

11. A ring according to claim 1, characterized in that the flexible strip (1), the compression chamber (2), and the female means (10, 10b) form a single piece made from the same plastics material.

12. A ring according to claim 1, characterized in that the compression chamber (2) extends over the entire periphery of the ring.

* * * * *

UNITED STATES PATENT AND TRADEMARK OFFICE
CERTIFICATE OF CORRECTION

PATENT NO. : 6,916,326 B2
DATED : July 12, 2005
INVENTOR(S) : Benchetrit

It is certified that error appears in the above-identified patent and that said Letters Patent is hereby corrected as shown below:

Column 7,
Line 9, insert -- to -- between "as" and "adjust".

Signed and Sealed this

Thirteenth Day of June, 2006

JON W. DUDAS
*Director of the United States Patent and Trademark Office*